United States Patent
Steinle et al.

(10) Patent No.: US 11,116,580 B2
(45) Date of Patent: Sep. 14, 2021

(54) SOLID-JOINT DEFORMATION-MODEL VERIFICATION

(71) Applicant: Brainlab AG, Munich (DE)

(72) Inventors: Wolfgang Steinle, Munich (DE); Christian Rabus, Munich (DE); Nils Frielinghaus, Heimstetten (DE)

(73) Assignee: BRAINLAB AG, Munich (DE)

( * ) Notice: Subject to any disclaimer, the term of this patent is extended or adjusted under 35 U.S.C. 154(b) by 630 days.

(21) Appl. No.: 15/573,766

(22) PCT Filed: Aug. 2, 2016

(86) PCT No.: PCT/EP2016/068436
§ 371 (c)(1),
(2) Date: Nov. 13, 2017

(87) PCT Pub. No.: WO2018/024322
PCT Pub. Date: Feb. 8, 2018

(65) Prior Publication Data
US 2018/0228549 A1 Aug. 16, 2018

(51) Int. Cl.
*A61B 34/20* (2016.01)
*G06F 30/23* (2020.01)
(Continued)

(52) U.S. Cl.
CPC ............ *A61B 34/20* (2016.02); *B25J 9/1692* (2013.01); *B25J 9/1697* (2013.01); *G06F 30/23* (2020.01);
(Continued)

(58) Field of Classification Search
None
See application file for complete search history.

(56) References Cited

U.S. PATENT DOCUMENTS 7,873,403 B2 * 1/2011 Lachner .................. G06T 17/10
345/420
9,101,282 B2 * 8/2015 Hartlep .................. A61B 5/055
(Continued)

FOREIGN PATENT DOCUMENTS

EP 2338432 B1 6/2011
KR 20150000269 A 1/2015

OTHER PUBLICATIONS

Russel H. Taylor, et al. "Computer-Intergrated Surgery: Technology and Clinical Application" Massachusetts Institute of Technology. 1996.
(Continued)

*Primary Examiner* — Joanne M Hoffman
(74) *Attorney, Agent, or Firm* — Middleton Reutlinger

(57) ABSTRACT

The present invention relates to computer-implemented medical method of verifying an expected deformation of an elastically deformable and actuator-adjusted medical fine-adjustment unit (1), the method comprising executing, on a processor of a computer, the steps of; —acquiring model data describing a model of the fine-adjustment unit (1), the model reflecting deformation properties of the fine-adjustment unit (1); —acquiring actuator data describing an actuator position of at least one actuator coupled to the fine-adjustment unit (1); —determining, based on the model data and the actuator data, target deformation data describing a target deformation of the fine-adjustment unit (1) caused by the at least one actuator at said actuator position; —acquiring actual deformation data describing an actual deformation of the fine-adjustment unit (1) caused by the at least one actuator at said actuator position; —determining, based on the target deformation data and the actual deformation data, verification data describing whether the target deformation corresponds to the actual deformation. The present invention further relates to a corresponding computer program causing (Continued)

a computer to perform such method, and a corresponding system comprising such a computer.

15 Claims, 4 Drawing Sheets

(51) Int. Cl.
- *G16H 40/40* (2018.01)
- *B25J 9/16* (2006.01)
- *G16H 50/50* (2018.01)
- *A61B 17/00* (2006.01)
- *A61B 90/00* (2016.01)
- *A61B 34/30* (2016.01)
- *A61B 34/10* (2016.01)

(52) U.S. Cl.
CPC ............ *G16H 40/40* (2018.01); *G16H 50/50* (2018.01); *A61B 34/30* (2016.02); *A61B 2017/00398* (2013.01); *A61B 2017/00725* (2013.01); *A61B 2034/102* (2016.02); *A61B 2034/2055* (2016.02); *A61B 2034/2059* (2016.02); *A61B 2034/2065* (2016.02); *A61B 2090/3966* (2016.02); *A61B 2090/3983* (2016.02)

(56) References Cited

U.S. PATENT DOCUMENTS

| | | | | |
|---|---|---|---|---|
| 9,125,690 B2* | 9/2015 | Wohlgemuth | ......... | A61B 6/547 |
| 9,336,590 B2* | 5/2016 | Stedele | ................. | G06T 7/0012 |
| 9,974,615 B2* | 5/2018 | Woerlein | ................ | A61B 5/061 |
| 2002/0099475 A1* | 7/2002 | Spangler | ................ | G05B 19/19 700/280 |
| 2004/0152972 A1* | 8/2004 | Hunter | ................. | A61B 17/025 600/424 |
| 2007/0055291 A1* | 3/2007 | Birkmeyer | ............. | A61B 90/13 606/130 |
| 2008/0201015 A1* | 8/2008 | Brogardh | ............... | B25J 9/1623 700/254 |
| 2010/0168763 A1* | 7/2010 | Zhao | ...................... | A61B 34/30 606/130 |
| 2011/0098553 A1* | 4/2011 | Robbins | ................. | A61B 5/055 600/410 |
| 2013/0204124 A1* | 8/2013 | Duindam | ............... | A61B 5/065 600/424 |
| 2016/0081754 A1* | 3/2016 | Kostrzewski | .......... | A61B 34/30 606/130 |
| 2018/0185113 A1* | 7/2018 | Gregerson | ........... | A61B 90/361 |

OTHER PUBLICATIONS

Duelen, et al. "Robot Calibration-Method and Results", Robotics and Computer Integrated Manufacturing, vol. 8, No. 4, pp. 223-231, Jan. 1991.

International Search Report and Written Opinion for PCT/EP2016/067436 dated Apr. 5, 2017.

European Patent Office: Priority Document of PCT/EP2015/073678 dated Oct. 13, 2015. 22 Pages.

* cited by examiner

SOLID-JOINT DEFORMATION-MODEL VERIFICATION

TECHNICAL FIELD

The present invention relates to a computer implemented method of verifying an expected deformation of an elastically deformable and actuator adjusted medical fine-adjustment unit, and to a corresponding system and computer program.

SUMMARY

Some recent medical procedures involve the use of solid-joint elements providing for a coupling between two structures, which are, even though these couplings are adjustable to a certain degree, free of play. In general, such solid-joint elements comprise at least one elastically deformable member connecting the elements which are to be coupled to each other. This elastic element may be deformed by at least one actuator, for example an electric stepper motor, connected to the elastic element such that in the end, the relative position (relative location and/or relative orientation) between the two elements can be adjusted with the help of the at least one motor. A specific type of such solid-joint element and a possible use thereof is described in the application PCT/EP2015/073678: This application describes a fine-adjustment unit coupling a trajectory guide for an elongated instrument, such as a biopsy needle, to a distal segment of an articulated support arm. By using this fine-adjustment unit, the longitudinal axis of the instrument held by the trajectory guide can be matched precisely to a planned trajectory. For determining the spatial position of the instrument held by the fine-adjustment unit, tracking markers are employed which are attached to the instrument or even to the fine-adjustment unit itself. As long as the tracking markers can be recognized by a corresponding medical tracking system, the spatial position of the instrument can be calculated by a medical navigation system. In this context, it is desirable to use such elastically deformable fine-adjustment units, which can be made from a plastic material, in places that prevent the use of conventional medical tracking measures: For example, confined places such as the gantry of CT-imaging devices cause line-of-sight issues that prevent the use of optical tracking systems.

The present invention provides a computer-implemented medical method that allows for using the above described solid-joint elements without the permanent need of using a medical tracking system.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The first aspect of the present invention relates to a computer-implemented medical method of verifying an expected deformation of an elastically deformable and actuator-adjusted medical fine-adjustment unit, the method comprising executing, on a processor of a computer, the steps of:

acquiring model data describing a model of the fine-adjustment unit, the model reflecting deformation properties of the fine-adjustment unit;

acquiring actuator data describing an actuator position of at least one actuator coupled to the fine-adjustment unit;

determining, based on the model data and the actuator data, target deformation data describing a target deformation of the fine-adjustment unit caused by the at least one actuator at said actuator position;

acquiring actual deformation data describing an actual deformation of the fine-adjustment unit caused by the at least one actuator at said actuator position;

determining, based on the target deformation data and the actual deformation data, verification data describing whether the target deformation corresponds to the actual deformation.

In other words, the present invention is to provide an adequate alternative to determine the position of structures of instruments that are held by the medical fine-adjustment unit. For that purpose, the core-aspect of the present invention is to verify whether expected bending or deforming characteristics of the fine-adjustment unit comply with the actual bending or deforming characteristics in reality. In the affirmative, a model reflecting deformation properties of the fine-adjustment unit can, as will be described further down below be used, to calculate the position of the fine-adjustment unit and any structure or instrument attached thereto with the help of a model, and without the need of any tracking system.

For verifying the expected deformation of the fine-adjustment unit in the first place, the actual deformation of the fine-adjustment unit has to be determined. For that purpose, acquiring the actual deformation data may involve determining the spatial position of at least one section of the fine-adjustment unit, by determining the spatial position of at least one tracking marker coupled directly or indirectly to the fine-adjustment unit, utilizing a medical tracking system; and/or by determining the spatial position of at least one fiducial coupled directly or indirectly to, or being part of the fine-adjustment unit, utilizing an imaging device.

Any medical tracking system, such as optical tracking systems, EM-tracking systems or ultrasound tracking systems may be used for that purpose, together with corresponding tracking markers. These tracking markers may be attached to the fine-adjustment unit itself and/or to any structure that is rigidly coupled to the fine-adjustment unit. For example, an actuator-housing provided at the distal end of an articulated support arm may be provided with tracking markers, as well. Furthermore, any object/instrument that is held by the fine-adjustment unit may be provided with tracking markers, as well.

As an additional or an alternative measure for determining the actual position of the fine-adjustment unit, imaging methods (including optical imaging, x-ray-imaging and the like) can be used so as to determine spatial position of any features of the fine-adjustment unit. For that purpose, dedicated features such as X-ray-visible markers or any significant features, for example intersection points of rods of the fine-adjustment unit or even structural features of the fine-adjustment unit which have been deliberately formed on or within the structure of the fine-adjustment unit (for example holes in the structure) may serve this purpose.

In a further embodiment, said target deformation data and said actual deformation data is determined for a plurality of different distinct actuator positions of the at least one actuator, particularly for a plurality of different actuator positions of a plurality of different actuators. Each actuator position corresponds to a particular deformation of the fine-adjustment unit.

Additionally or alternatively and according to a further embodiment, said target deformation data and said actual deformation data is determined for a continuum of actuator positions of the at least one actuator, particularly for a continuum of actuator positions of a plurality of different actuators.

Furthermore, a permutation of all actuator positions of all actuators may be determined, wherein the actuator position of only one actuator is changed at a time, while the actuator positions of the remaining actuators remain unchanged, particularly wherein the plurality of different distinct actuator positions and/or the continuum of actuator positions of the plurality of different actuators represent(s) the whole motion range of the fine-adjustment unit.

The number of actuator positions to be acquired can be predetermined by defining a number of extreme or intermediate positions representing the whole parameter space e. g. by dividing the actuator position range into a number of segments of equal size in each dimension and either forming a permutation of all these actuator positions or changing only the position of one actuator at a time while leaving the other dimensions steady.

After it has been checked whether the target deformation sufficiently corresponds to the actual deformation for each of the actuator position(s), said verification data may be transmitted to a user interface, indicating whether the target deformation sufficiently corresponds to the actual deformation. Moreover, information as to the target deformation (e.g. actual value) and the actual deformation (e.g. actual value), specifically information as to a deviation of the actual deformation from the target deformation may be indicated.

In other words, it is indicated to the user, for example optically via a user interface which may comprise a display unit, whether the calculation based upon the model of the fine-adjustment unit satisfactorily reflects the deformation of the fine-adjustment unit in reality.

In this context, at least one threshold may be set which must not be exceeded by the determined deviation. For example, it may be indicated to a user that a pre-set deviation threshold has been exceeded, whereupon a user input may be requested as to whether the determined deviation is acceptable.

For example, large deviations may be an indication that the fine-adjustment unit is defective and should be replaced. On the other hand however, if the determined deviation is rather small and within an acceptable tolerance, at least one parameter of the model of the fine-adjustment unit may be adjusted such that the recalculated target deformation corresponds to the actual deformation. In other words, the model may be adapted to exactly reflect the determined actual deformation, resulting in a "calibration" of the fine-adjustment unit model. In this context, an optimization procedure of the model may be performed, comprising optimization algorithms, such as the damped least-squares method, wherein the Route Mean Square (RMS) of the difference of the calculated and the determined position is the criteria to be optimized.

As soon as the model of the fine-adjustment unit accurately reflects the actual deformation of the fine-adjustment unit, the at least one actuator coupled to the fine-adjustment unit may be controlled on the basis of the calibrated model of the fine-adjustment unit. Consequently, the deformation of the fine-adjustment unit and therefore also the spatial position of an instrument held by the fine-adjustment unit can be determined with the help of the model and the determined position of the at least one actuator provided to deform the fine-adjustment unit. For that reason, tracking measures are not necessary anymore, so that the fine-adjustment unit can be employed even when tracking systems cannot be used, for example if an undisrupted line-of-sight between optical tracking cameras and the fine-adjustment unit is not possible.

Particularly in cases where motors having no absolute encoder, such as brushless DC-motors or stepper-motors are used as actuators for deforming the fine-adjustment unit, the above described "calibration"-procedure may be performed during an initialization run of the motors prior to the use of the fine-adjustment unit. Additionally or alternatively, the "calibration"-procedure may be performed during the use of the fine-adjustment unit, for example each time when the instrument is changed. Furthermore, the "calibration"-procedure could be performed at any point in time on demand of the user who may be unsure about the accuracy of the fine-adjustment unit.

The above described model of the fine-adjustment unit may be a kinematic model representing or approximating movement characteristics of the fine-adjustment unit, particularly as at least one circular segment or a polynomial function. The model may be also a model comprising at least one mass-spring-system for the fine-adjustment unit and may also be a FEM-model.

A further aspect of the present invention relates to a computer program which, when running on a computer, causes the computer to perform any of the above-described method steps, and/or a program storage medium on which such program is stored, particularly in a non-transitory form.

A further aspect of the present invention relates to a system for verifying an expected deformation of an elastically deformable and actuator-adjusted medical fine-adjustment unit, comprising a computer on which the above described program is stored and/or run. An embodiment of such system may comprise the medical fine-adjustment unit which may in particular be provided at a distal segment of an articulated support arm that comprises a plurality of aligned segments which are adjustably coupled to each other via rotational and/or ball-joints.

Definitions

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

The invention also relates to a navigation system for computer-assisted surgery, comprising:

the computer of the preceding claim, for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a (tracking) marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single (tracking) marker or a plurality of (individual) (tracking) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows to determine the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

BRIEF DESCRIPTION OF DRAWINGS

In the following, the invention is described with reference to the enclosed figures which represent preferred embodiments of the invention. The scope of the invention is however not limited to the specific features disclosed in the figures, which show.

DETAILED DESCRIPTION

Figure 1:
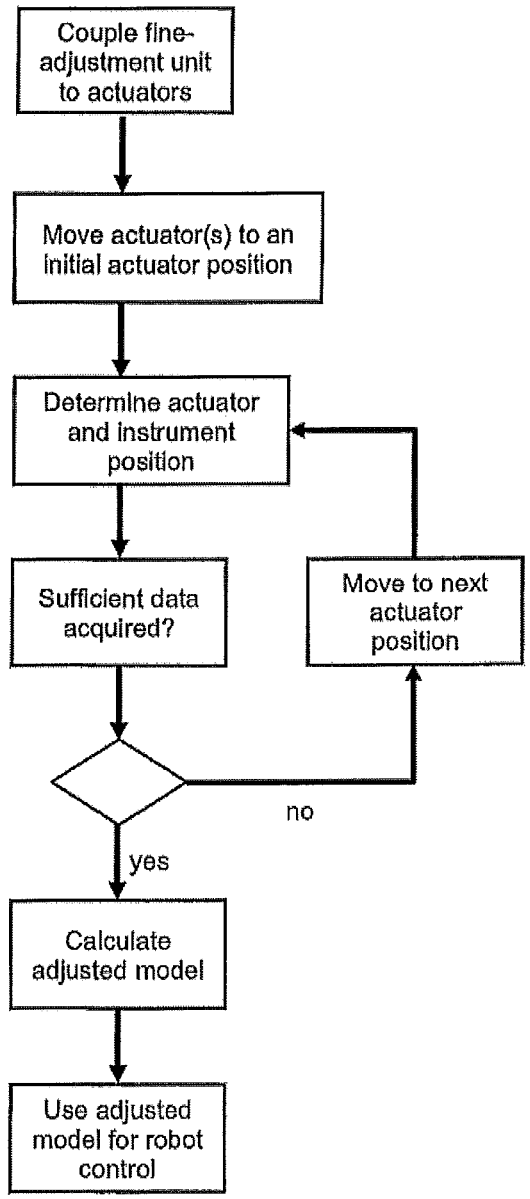
FIG. 1 an embodiment of the inventive verification-method.

FIG. 1 shows an embodiment of the inventive verification-method: First of all, the fine-adjustment unit 1 is coupled to actuators (not shown; disposed within the housing at the distal segment 4 of the support arms) that will be used to deform the fine-adjustment unit 1 so as to adjust the position of an instrument with respect to a distal segment 4 of an articulated support arm 5 (shown in FIG. 2). In a subsequent step, a "calibration"-procedure is performed by moving the actuators to an initial actuator position, whereupon the initial actuator position is determined with the help of sensors connected to the actuators. Additionally, the spatial position of the instrument is determined, with the actuators in their initial position, by means of a medical tracking system comprising the camera array 3. After that, the actuators are moved to a pre-determined number of positions, such that the fine-adjustment unit is correspondingly deformed, wherein, for each position of the actuators, the deviation between the determined actual deformation and the calculated target deformation is determined. After that determination for each position of the actuators, it is decided whether or not sufficient data has been acquired, for making a reliable statement as to whether or not the model sufficiently reflects the actual deformation properties of the fine-adjustment unit.

Following that step, it can be decided whether or not to discard the fine-adjustment unit, or, in case the deviation is rather small, to adjust the model such that the calculated deformation properties perfectly match the actual deformation properties.

Subsequent to that "calibration"-procedure, the fine-adjustment unit can be used in medical procedures, wherein it's deformation and consequently the spatial position of an instrument attached to the fine-adjustment unit can be calculated precisely.

Figure 2:
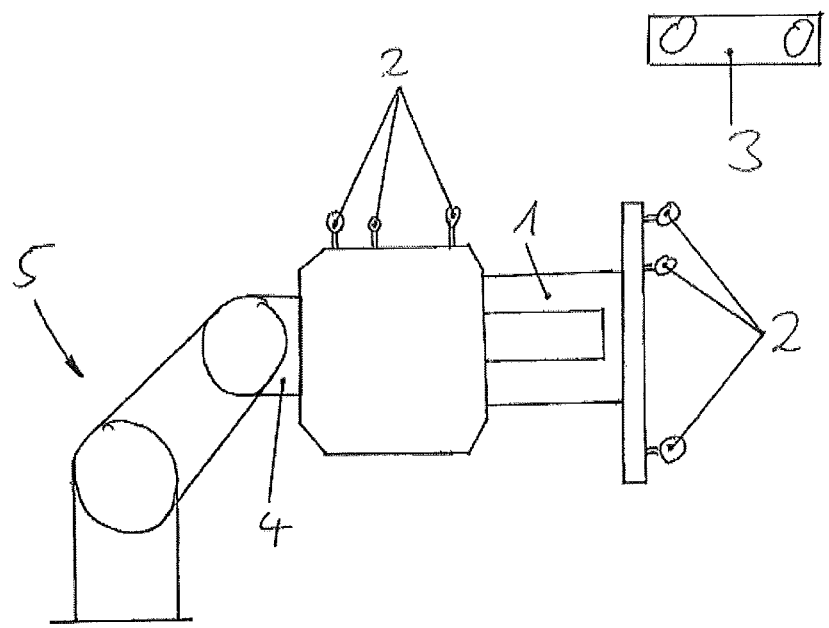
FIG. 2 an embodiment of the inventive system comprising a fine-adjustment unit.

FIG. 2 schematically shows a fine-adjustment unit 1 at the distal segment 4 of an articulated support arm 5. The fine-adjustment unit 1 adjustably couples an instrument at it's distal end to a actuator housing at it's proximal end. Both, the actuator-housing and the instrument are each provided with a plurality of tracking markers 2 which are recognized by a camera array 3 of an optical medical tracking system. As soon as the model of the fine-adjustment unit 1 is calibrated, the tracking markers 2 at the instrument can be removed as they are not needed any more for determining the spatial position of the instrument. Rather, the spatial position of the instrument can be calculated by determining the spatial position of the tracking markers 2 at the actuator-housing, and by calculating, based on the "calibrated" model of the fine-adjustment unit and the determined position of each actuator, the relative position between these tracking markers and the instrument. However, the tracking markers 2 may also remain at the instrument, thereby providing a further, redundant measure to determine the spatial position of the instrument.

Figure 3:
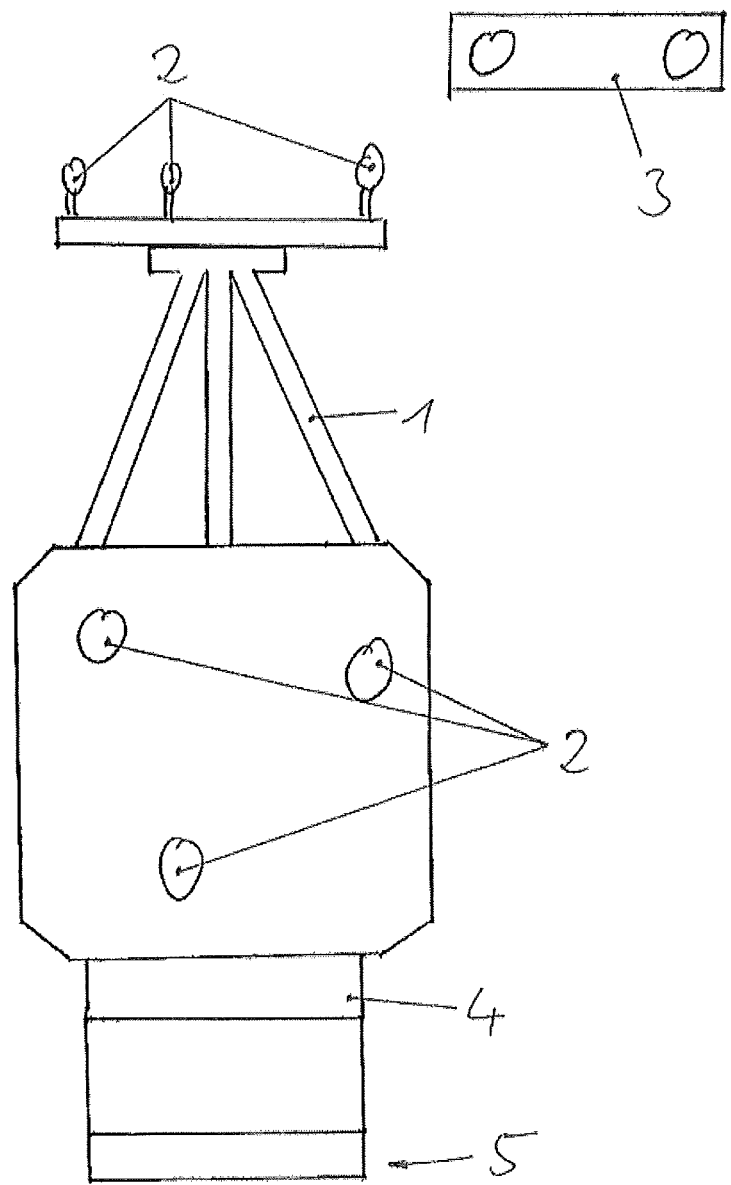
FIG. 3 a top-view onto the embodiment shown in FIG. 2 in an undeformed state of the fine-adjustment unit.
Figure 4:
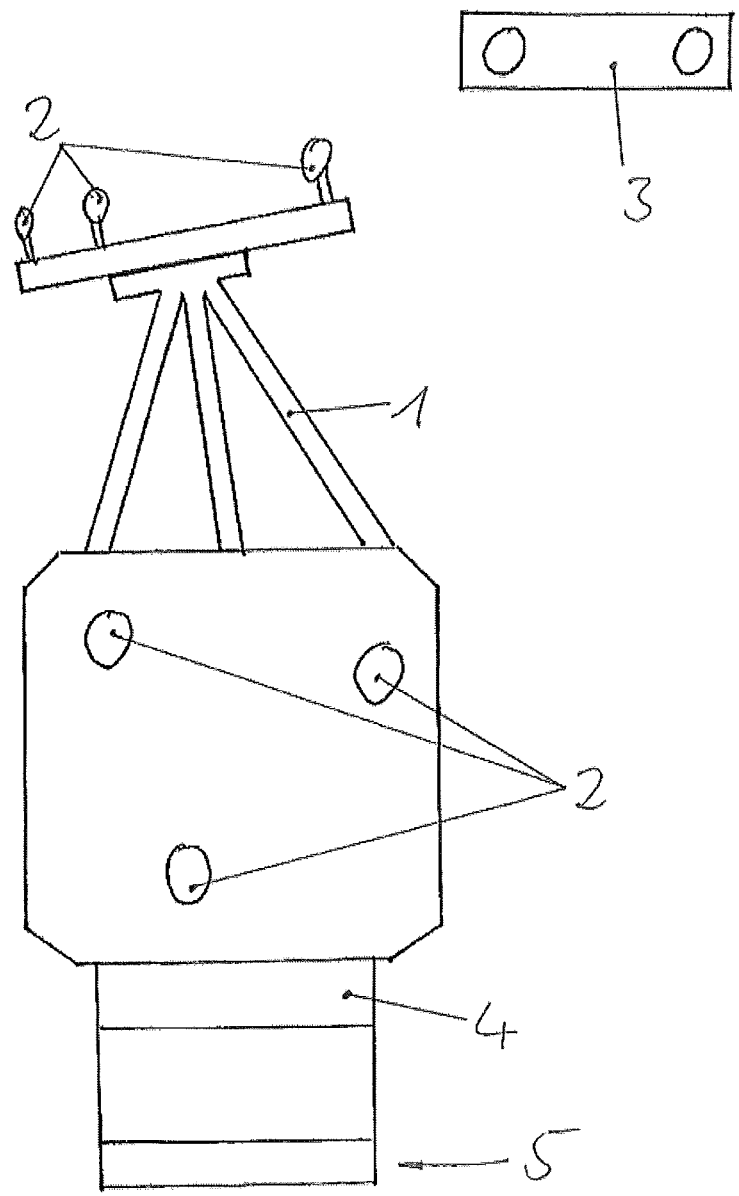
FIG. 4 a top-view onto the embodiment shown in FIG. 2 in a deformed state of the fine-adjustment unit.

It becomes apparent from FIGS. 3 and 4, that the relative position between the instrument and the distal segment 4 of the articulated arm 5 is adjusted by an actuator-induced deformation of the fine-adjustment unit 1.

The invention claimed is:

1. A computer-implemented method comprising executing, on at least one processor, the steps of:
   acquiring model data describing a model of a fine-adjustment unit, the fine-adjustment unit being positioned between a distal segment of an articulated support arm and an instrument and having at least one elastically deformable member connecting the articulated support arm and the instrument, the at least one elastically deformable member deformed by at least one actuator connected to the at least one elastically deformable member to adjust relative spatial position of the instrument and the articulated support arm, the model reflecting elastic deformation properties of the fine-adjustment unit;
   acquiring actuator data describing an actuator position of the at least one actuator coupled to the fine-adjustment unit;
   determining, based on the model data and the actuator data, target deformation data describing a target deformation of the fine-adjustment unit caused by the at least one actuator at the actuator position wherein each actuator position corresponds to a particular deformation of the fine-adjustment unit;
   acquiring actual deformation data describing an actual deformation of the fine-adjustment unit caused by the at least one actuator at the actuator position, wherein each actuator position corresponds to a particular deformation of the fine-adjustment unit;
   determining, based on the target deformation data and the actual deformation data, verification data describing whether the target deformation corresponds to the actual deformation.

2. The method according to claim 1, wherein acquiring the actual deformation data involves determining a spatial position of at least one section of the fine-adjustment unit, by
   determining spatial position of at least one tracking marker coupled directly or indirectly to the fine-adjustment unit, utilizing a medical tracking system; and/or by
   determining spatial position of at least one fiducial coupled directly or indirectly to, or being part of the fine-adjustment unit, utilizing an imaging device.

3. The method according to claim 2, wherein the target deformation data and the actual deformation data is determined for a plurality of different distinct actuator positions of the at least one actuator.

4. The method according to claim 3, wherein the target deformation data and the actual deformation data is determined for a continuum of actuator positions of the at least one actuator.

5. The method according to claim 4, wherein at least two actuators are coupled to the fine-adjustment unit, and wherein a permutation of all actuator positions of the at least two actuators is determined, wherein the actuator position of only one actuator is changed at a time, while the actuator positions of the remaining actuators remain unchanged, and further wherein the plurality of different distinct actuator positions and/or the continuum of actuator positions of the at least two actuators represent(s) the whole motion range of the fine-adjustment unit.

6. The method according to claim 1, wherein the verification data is transmitted to a user interface indicating whether the target deformation corresponds to the actual deformation, and further wherein information as to the target deformation and the actual deformation, is indicated.

7. The method according to claim 6, wherein a user input is requested as to whether a determined deviation of the actual deformation from the target deformation is acceptable.

8. The method according to claim 6, wherein, based on the verification data, at least one parameter of the model of the fine-adjustment unit is adjusted such that the target deformation corresponds to the actual deformation.

9. The method according to claim 8, wherein a control of the at least one actuator is based on the model comprising the at least one adjusted parameter.

10. The method according to claim 8, wherein adjusting at least one parameter of the model involves applying an optimization procedure of a plurality of model parameters for achieving an optimized combined error value.

11. The method according to claim 1, wherein the verification data is determined during an initialization procedure prior to utilization of the fine-adjustment unit, and/or during utilization of the fine-adjustment unit.

12. The method according to claim 1, wherein the model is selected from a group consisting of:
    a kinematic model representing or approximating movement characteristics of the fine-adjustment unit;
    a model comprising at least one mass-spring-system; and
    a FEM-model.

13. A non-transitory computer-readable storage medium comprising instructions stored thereon which, when running on at least one processor of at least one computer, causes the at least one processor to perform the steps of:
    acquiring model data describing a model of a fine-adjustment unit, the fine-adjustment unit being positioned between a distal segment of an articulated support arm and an instrument and having at least one elastically deformable member connecting the articulated support arm and the instrument, the at least one elastically deformable member deformed by at least one actuator connected to the at least one elastically deformable member to adjust relative spatial position of the instrument and the articulated support arm, the model reflecting elastic deformation properties of the fine-adjustment unit;
    acquiring actuator data describing an actuator position of the at least one actuator coupled to the fine-adjustment unit;
    determining, based on the model data and the actuator data, target deformation data describing a target deformation of the fine-adjustment unit caused by the at least one actuator at the actuator position wherein each actuator position corresponds to a particular deformation of the fine-adjustment unit;
    acquiring actual deformation data describing an actual deformation of the fine-adjustment unit caused by the at least one actuator at the actuator position, wherein each actuator position corresponds to a particular deformation of the fine-adjustment unit;
    determining, based on the target deformation data and the actual deformation data, verification data describing whether the target deformation corresponds to the actual deformation.

14. A system to verify a deformation of an elastically deformable and actuator-adjusted medical fine-adjustment unit, comprising at least one processor on at least one computer having associated memory, the associated memory having instructions, which when executed by the at least one processor causes the at least one processor to perform the steps comprising:

acquire model data describing a model of a fine-adjustment unit, the fine-adjustment unit being positioned between a distal segment of an articulated support arm and an instrument and having at least one elastically deformable member connecting the articulated support arm and the instrument, the at least one elastically deformable member deformed by at least one actuator connected to the at least one elastically deformable member to adjust relative spatial position of the instrument and the articulated support arm, the model reflecting elastic deformation properties of the fine-adjustment unit;

acquire actuator data describing an actuator position of at least one actuator coupled to the fine-adjustment unit;

determine, based on the model data and the actuator data, target deformation data describing a target deformation of the fine-adjustment unit caused by the at least one actuator at the actuator position wherein each actuator position corresponds to a particular deformation of the fine-adjustment unit;

acquire actual deformation data describing an actual deformation of the fine-adjustment unit caused by the at least one actuator at the actuator position;

determine, based on the target deformation data and the actual deformation data, verification data describing whether the target deformation corresponds to the actual deformation.

15. The system of claim 14, further comprising the medical fine-adjustment unit which is provided at the distal segment of the articulated support arm comprising a plurality of aligned segments adjustably coupled to each other.

* * * * *